US006198003B1

(12) United States Patent
Lin et al.

(10) Patent No.: US 6,198,003 B1
(45) Date of Patent: *Mar. 6, 2001

(54) METHOD FOR PRODUCING ALKYL MERCAPTANS AND/OR DIALKYL MONOSULFIDES

(75) Inventors: Kaung-Far Lin; James E. Boone, both of Baton Rouge; Michael D. Matthews, Walker; John C. Prindle, Jr.; Sharon D. Booth McGee, both of Baton Rouge, all of LA (US)

(73) Assignee: Albemarle Corporation, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/295,622

(22) Filed: Apr. 20, 1999

(51) Int. Cl.[7] .................. C07C 319/08; C07C 319/16
(52) U.S. Cl. .................. 568/71; 568/61; 568/38
(58) Field of Search .................. 568/59, 38, 69, 568/70, 71

(56) References Cited

U.S. PATENT DOCUMENTS

| | | | |
|---|---|---|---|
| 2,667,515 | 1/1954 | Beach et al. | 260/609 |
| 2,796,438 | 6/1957 | Martin et al. | 260/609 |
| 2,816,146 | 12/1957 | Doumani | 260/609 |
| 2,820,060 | 1/1958 | Folkins et al. | 260/609 |
| 2,820,062 | 1/1958 | Folkins et al. | 260/609 |
| 2,820,831 | 1/1958 | Doumani | 260/609 |
| 2,822,400 | 2/1958 | Cinque et al. | 260/609 |
| 2,822,401 | 2/1958 | Hoot et al. | 260/609 |
| 2,951,872 | 9/1960 | Folkins et al. | 260/609 |
| 2,951,873 | 9/1960 | Folkins et al. | 260/609 |
| 3,548,007 | 12/1970 | Comte | 260/609 |
| 3,697,602 | 10/1972 | Schreyer et al. | 260/609 R |
| 3,935,276 | 1/1976 | Biola et al. | 260/609 R |
| 4,302,605 | 11/1981 | Buchholz et al. | 568/60 |
| 5,283,369 | * 2/1994 | Clark | 568/71 |
| 5,733,836 | 3/1998 | Stinn et al. | 502/255 |
| 5,866,721 | * 2/1999 | Hofen | 568/71 |

OTHER PUBLICATIONS

Mashkina, et al., "Effect of Acid–Base Properties of Catalysts on Their Activity in Methylmercaptane Synthesis", React. Kinet. Catal. Lett., vol. 34, No. 2, 1987, pp. 407–412.

Mashkin, V. Yu, "Kinetic Study of Dimethylsulfide and Methanethiol Synthesis", Applied Catalysis A: General, 1994, vol. 109, pp. 45–61.

Folkins, et al., "Role of the Catalyst in the Reaction of Alcohols and Hydrogen Sulfide", Proc. Am. Petrol. Inst., vol. 42, Sect. III, 1962, pp. 188–196.

Miki, et al., "Catalysts for the Synthesis of Methyl Mercaptan and Dimethyl Sulfide", Yuki Gosei Kagaku, 1966, vol. 24, No. 6, pp. 471–475.

Stull, D.R., et al., "The Chemical Thermodynamics of Organic Compounds", Robert E. Kreger Publishing Company, Malabar, Florida, 1987, pp. 137, 139, 219, 229, 230, 245, 422, 563, 611.

Folkins, H.O., et al., "Synthesis of Mercaptans", I & EC Process Design and Development, 1962, vol. 1, pp. 271–276.

Lavalley, Jean–Claude et al., "Infrared Study of Coadsorption of $H_2S$ and $CO_2$ on γ–Alumina", J.C. S. Chem. Comm., 1979, pp. 146–148.

Mashkin, Viktor Yu et al., "Kinetics of Catalytic Reaction between Methanol and Hydrogen Sulfide", Ind. Eng. Chem. Res., 1995, vol. 34(9), pp. 2964–2970.

Mashkina, A. V., "Heterogeneous catalytic synthesis of alkanethiols and dialkyl sulfides from alcohols and hydrogen sulfide", Russian Chemical Reviews, 1995, vol. 64(12), pp. 1131–1147.

Suckow, M., et al., "Optimized adsorptive gas–desulphurization by mathematical modeling", Separation Technology, edited by E.F. Vansant, 1994, Elsevier Science B.V., pp. 143–151.

* cited by examiner

*Primary Examiner*—Jean F. Vollano
(74) *Attorney, Agent, or Firm*—Philip M. Pippenger

(57) ABSTRACT

A highly efficient method of producing alkyl mercaptan and/or dialkyl monosulfides which involves employing carbon dioxide as an internal coolant is described. Only negligible amounts of carbonyl sulfide were formed. In addition, relatively easy separation of carbon dioxide from the reaction mixture facilitates an efficient coolant recycle process, giving a simple and effective mode of temperature control.

31 Claims, No Drawings

METHOD FOR PRODUCING ALKYL MERCAPTANS AND/OR DIALKYL MONOSULFIDES

TECHNICAL FIELD

This invention pertains to a novel, highly efficient method for the production of alkyl mercaptan and dialkyl monosulfides.

BACKGROUND

Alkyl mercaptan and dialkyl monosulfides are useful as intermediates in the production of various end products. For example, methionine, an important component in poultry feed, can be prepared in a relatively cost-efficient manner using methyl mercaptan prepared pursuant to this invention.

The reaction of alkanols and hydrogen sulfide in the presence of catalytic materials to produce alkyl mercaptan and dialkyl monosulfides has been known for almost ninety years. Modern commercial methods for the production of alkyl mercaptan and dialkyl monosulfides from alkanols and hydrogen sulfide generally employ alumina-based catalysts. As the reaction rate in the presence of these modern catalysts is quite high and the reactions themselves are extremely exothermic, heat is generated at a high rate. In addition, the reaction rate rises with temperature, thus in the absence of efficient cooling, a small temperature rise may be quickly amplified. It is therefore desirable to employ a cooling method which has not only a high heat removal capacity, but also the ability to quickly stabilize the reaction temperature in the event of even a small temperature rise.

Some present commercial methods of producing methyl mercaptan and dimethyl sulfide utilize an evaporative cooling method by supplying methanol as a liquid/vapor mixture. However, in practice, fine control of reaction temperature is limited by the difficulty in providing precise mixtures and altering said mixtures quickly and accurately. Furthermore, such methods strongly recommend the partitioning of the reaction zone into smaller regions in order to obtain sufficient cooling efficiency.

Other cooling methods utilized in modern commercial processes involve a non-adiabatic transfer of heat across an interface to an external coolant. The hot reaction products transfer heat to the cooling medium only indirectly through an intermediate separator. Reactors so cooled are susceptible to spatially uneven cooling, leading to "hot spots" which can dramatically reduce the life of the catalyst. In addition, the inability of coolant and reactant molecules to mix, as well as the indirectness of reactant-coolant heat transfer force a thermodynamic limitation on the rate and energy-efficiency of cooling attainable with such methods. As a result, the ability to respond quickly and efficiently to small temperature changes is also limited. Such non-adiabatic reactor designs are also significantly more expensive than simpler adiabatic designs.

Furthermore, sources of hydrogen sulfide tapped for industrial use can contain very high amounts of contaminants. In particular, carbon dioxide can be present in amounts of 50% by mole or higher. Carbon dioxide and hydrogen sulfide react efficiently in the presence of aluminum oxide catalysts to form another contaminant, carbonyl sulfide (J. Lavalley et al. *J. C. S. Chem. Comm.* 1979, pgs. 146–148)—at high carbon dioxide to hydrogen sulfide ratios, the formation of carbonyl sulfide is deemed very likely (M. Suckow et al. *Separation Technology* 1994, pgs. 143–151). In order to produce a product of acceptable purity, it would seem advisable to remove the carbon dioxide contaminant before the reaction process is carried out. However, not only does separation of carbon dioxide from reactants of similar weights and vapor pressures require time and energy, but once removed, the resultant carbon dioxide is a resource which may be wasted unless the costly steps of storing it and/or transporting it to another utility are undertaken.

It would thus be a significant advance in the state of the art if a process for producing alkyl mercaptan and/or dialkyl monosulfides could be found which has among its benefits increased cooling efficiency, improved capacity to respond quickly and efficiently to temperature changes, simple reactor design and beneficial utilization of the carbon dioxide contaminant, while maintaining a high rate and quality of product output.

SUMMARY OF THE INVENTION

A process has been devised which can achieve the above-mentioned benefits while providing for high-yield, carbonyl sulfide-free production of alkyl mercaptan and/or dialkyl monosulfides. It has been found, pursuant to this invention, that when carbon dioxide gas is used as an internal coolant in the aluminum oxide catalyzed reaction of alkanols and hydrogen sulfide to produce alkyl mercaptan and dialkyl monosulfides, a surprisingly low, often undetectable amount of carbonyl sulfide is formed.

Additionally, the direct contact and complete mixing of the hot reaction product with the coolant increases the rate and energy efficiency of cooling. If the carbon dioxide-hydrogen sulfide concentration ratio supplied to the reaction zone is raised/lowered in response to temperature increase/decrease, a highly responsive mode of reaction zone temperature control can be realized.

Also, the internal usage of carbon dioxide allows the reaction to be carried out in a simple adiabatic reactor. Expensive designs which require partitioning of reaction zone and external coolants are thus eliminated.

Furthermore, the separation of carbon dioxide from the vapor phase product mixture is generally easier than separation from the vapor phase reaction mixture due to increased weight and decreased vapor pressure of products relative to reactants.

Accordingly, in one of its embodiments, this invention provides a process for producing alkyl mercaptan and/or dialkyl monosulfide, which process comprises:

A) continuously introducing into a reaction zone components comprising (i) an alkanol, (ii) hydrogen sulfide, and (iii) carbon dioxide to form a vapor phase reaction mixture and contacting said mixture in said reaction zone with a solid phase catalyst such that a vapor phase product mixture comprising alkyl mercaptan and/or dialkyl monosulfide is formed; and B) continuously withdrawing from said reaction zone a mixture comprising alkyl mercaptan and/or dialkyl monosulfides.

The carbon dioxide may already be present in the feed stream of one or both of the reactants. After functioning as a coolant in the reaction, the carbon dioxide can be separated from the heavier alkyl mercaptan and dialkyl monosulfide reaction products, cooled, and reintroduced into the reactor with incoming reactants to give continued cooling benefits. The repeated removal and recycling of carbon dioxide can be used to increase the amount of carbon dioxide relative to hydrogen sulfide, resulting in an increased cooling capacity.

If a reactant stream contains carbon dioxide, it may be desirable to achieve elevated carbon dioxide levels by separating it from the vapor phase product mixture, cooling it, and reusing it without employing any additional sources of carbon dioxide. However, a source of fresh carbon dioxide can be used instead of or in addition to the recycled carbon dioxide. By "fresh", it is meant that the carbon dioxide comes from a source independent of the present process. Thus, it may be desirable to begin the process with fresh carbon dioxide as the coolant, and decrease its amount as a recycled stream is generated. If a reactant source contains carbon dioxide, dependence upon fresh carbon dioxide can be reduced more quickly.

Highly sensitive temperature control can be realized by the adjustment of reactor input of recycled and/or fresh carbon dioxide. Typically, temperature control at a constant reactor pressure is effected by altering the mole ratios of carbon dioxide to reactants introduced into the reaction zone.

Thus, in another embodiment, this invention provides a process for producing alkyl mercaptan and/or dialkyl monosulfide, which process comprises:

A) continuously introducing into a reaction zone components comprising (i) an alkanol, (ii) hydrogen sulfide, and (iii) carbon dioxide to form a vapor phase reaction mixture and contacting said mixture with a solid phase catalyst such that a vapor phase product mixture comprising alkyl mercaptan and/or dialkyl monosulfide and carbon dioxide is formed in said reaction zone;

B) continuously withdrawing such vapor phase product mixture from said reaction zone;

C) separating carbon dioxide from said withdrawn vapor phase product mixture; and D) recycling carbon dioxide from C) to A).

Both of the above embodiments can be characterized by the following. Preferably, the mole ratio of (i) to (ii) introduced into the reaction zone is in the range of about 0.5 mole of (i) per mole of (ii) to about 2.5 moles of (i) per mole of (ii), and the mole ratio of (ii) to (iii) introduced into the reaction zone is in the range of about 0.2 mole of (ii) per mole of (iii) to about 1 mole of (ii) per mole of (iii). The pressure in the reaction zone is typically in the range of about 15 psia to about 500 psia. The temperature in the reaction zone is preferably in the range of about 250° C. to about 450° C. A typical catalytic medium is a composition comprised of (I) aluminum oxide, (II) potassium oxide, and (III) tungsten oxide, wherein the weight ratio of (II) to (I) is in the range of about 0 gram of (II) per gram of (I) to about 0.05 gram of (II) per gram of (I), and the weight ratio of (III) to (I) is in the range of about 0 gram of (III) per gram of (I) to about 0.12 gram of (III) per gram of (I). It is preferable that the catalyst have a surface area in the range of about 100 to about 300 square meters per gram of catalyst. A typical vapor space time is in the range of about 0.01 to about 100 seconds, wherein the vapor space time is defined to be the volume of the empty reaction zone divided by the reaction mixture volumetric flow rate.

In an additional embodiment, this invention provides a process for making alkyl mercaptan, which process comprises:

A) continuously introducing into a reaction zone components comprising (i) an alkanol, (ii) hydrogen sulfide, and (iii) carbon dioxide to form a vapor phase reaction mixture, and contacting said mixture in said reaction zone with a solid phase catalyst such that a vapor phase product mixture comprising alkyl mercaptan is formed; and B) continuously withdrawing from said reaction zone a mixture comprising alkyl mercaptan.

Preferably, the ratio of (i) to (ii) introduced into the reaction zone is in the range of about 0.5 mole of (i) per mole of (ii) to about 1.25 mole of (i) per mole of (ii), wherein the mole ratio of (ii) to (iii) introduced into the reaction zone is in the range of about 0.2 mole of (ii) per mole of (iii) to about 1 mole of (ii) per mole of (iii), wherein the catalyst is a composition comprised of (I) γ-aluminum oxide, (II) potassium oxide ($K_2O$), and (III) tungsten oxide ($WO_3$), wherein the weight ratio of (II) to (I) is in the range of about 0 gram of (II) per gram of (I) to about 0.05 gram of (II) per gram of (I), and wherein the weight ratio of (III) to (I) is in the range of about 0 gram of (III) per gram of (I) to about 0.12 gram of (III) per gram of (I), such that at least 10 mole percent of said vapor phase product mixture is alkyl mercaptan.

In yet another embodiment, this invention provides a process for making dialkyl monosulfides, which process comprises:

A) continuously introducing into a reaction zone components comprising (i) an alkanol, (ii) hydrogen sulfide, and (iii) carbon dioxide to form a vapor phase reaction mixture and contacting said mixture in said reaction zone with a solid phase catalyst such that a vapor phase product mixture comprising dialkyl monosulfide is formed; and B) continuously withdrawing from said reaction zone a mixture comprising dialkyl monosulfide.

Preferably, the mole ratio of (i) to (ii) fed into the reaction zone is in the range of about 1 mole of (i) per mole of (ii) to about 2.5 moles of (i) per mole of (ii), wherein the mole ratio of (ii) to (iii) fed into the reaction zone is in the range of about 0.2 mole of (ii) per mole of (iii) to about 1 mole of (ii) per mole of (iii), wherein the catalyst is a composition comprised of (I) γ-aluminum oxide, (II) potassium oxide ($K_2O$), and (III) tungsten oxide ($WO_3$), wherein the weight ratio of (II) to (I) is in the range of about 0 gram of (II) per gram of (I) to about 0.02 gram of (II) per gram of (I), wherein the weight ratio of (III) to (I) is in the range of about 0 gram of (III) per gram of (I) to about 0.04 gram of (III) per gram of (I), such that at least 10 mole percent of said vapor phase product mixture is dialkyl monosulfide.

The above and other embodiments will be apparent from the ensuing description and appended claims.

The alkanols utilized in the practice of this invention can be unsubstituted or they can be substituted with functional groups which permit or facilitate the nucleophilic attack of the hydrosulfide anion ($SH^-$) on the carbon atom to which the alkanol oxygen atom is attached. Suitable alkanols include: methanol, ethanol, propanol, isopropanol, 1-butanol, 2-butanol, isobutanol, tert-butanol, pentanol, 2-pentanol, 3-pentanol, 2-heptanol, 3-nonanol, 4-decanol, methoxymethanol, ethoxymethanol, 2-ethoxy-1-ethanol, 3-propoxy-1-propanol, 1-propoxy-1-propanol, 2-methoxy-2-butanol, 2-ethoxy-1-pentanol, 5-ethoxy-1-pentanol, 5-propoxy-2-heptanol, 4-ethoxy-1-octanol, 4-propoxy-2-decanol, hydroxymethamine, 2-amino-1-ethanol, 3-amino-1-propanol, 4-amino-2-pentanol, 5-amino-1-heptanol, 6-amino-2-nonanol etc. Preferably an unsubstituted alkanol is used. More preferably, an unsubstituted alkanol of less than about twelve carbon atoms is used. Most preferably, methanol is used.

It is preferable to have a mole ratio of alkanol to hydrogen sulfide in the range of about 0.5 mole of alkanol per mole of hydrogen sulfide to about 2.5 moles of alkanol per mole of hydrogen sulfide. Is it has been found that the relative proportions of alkyl mercaptan and dialkyl monosulfide produced in the process of this invention vary with the relative proportions of alkanol and hydrogen sulfide fed into the reaction zone. In order to produce alkyl mercaptan in greater molar amounts with respect to dialkyl monosulfide, it is desirable to have a mole ratio of alkanol to hydrogen sulfide in the range of about 0.5 mole of alkanol per mole of hydrogen sulfide to about 1.25 moles of alkanol per mole of hydrogen sulfide. A mole ratio in the range of about 0.9 mole of alkanol per mole of hydrogen sulfide to about 1.1 mole of alkanol per mole of hydrogen sulfide is most desirable for producing larger molar amounts of alkyl mercaptan with respect to dialkyl monosulfide. In order to produce dialkyl monosulfide in larger molar amounts than alkyl mercaptan, it is desirable to have a mole ratio of alkanol to hydrogen sulfide in the range of about 1 mole of alkanol per mole of hydrogen sulfide to about 2.5 moles of alkanol per mole of hydrogen sulfide. A mole ratio in the range of about 1.9 moles of alkanol per mole of hydrogen sulfide to about 2.1 moles of alkanol per mole of hydrogen sulfide is most desirable for producing dialkyl monosulfide in greater molar abundance than alkyl mercaptan.

In conducting the process of this invention, it is preferable that carbon dioxide be used in amounts such that the temperature in the reaction zone is effectively controlled. Thus it is preferable that the mole ratio of hydrogen sulfide to carbon dioxide be in the range of about 0.2 mole of hydrogen sulfide per mole of carbon dioxide to about 1 of hydrogen sulfide per mole of carbon dioxide. It is more preferable that the mole ratio of hydrogen sulfide to carbon dioxide be in the range of about 0.2 mole of hydrogen sulfide per mole of carbon dioxide to about 0.8 mole of hydrogen sulfide per mole carbon dioxide. If a molar predominance of alkyl mercaptan is desired, it is most preferable that the mole ratio of hydrogen sulfide to carbon dioxide be in the range of about 0.4 mole of hydrogen sulfide per mole of carbon dioxide to about 0.6 mole of hydrogen sulfide per mole of carbon dioxide. If a molar predominance of dialkyl monosulfide is desired, it is most preferable that the mole ratio of hydrogen sulfide to carbon dioxide be in the range of about 0.2 mole of hydrogen sulfide per mole of carbon dioxide to about 0.4 mole of hydrogen sulfide per mole of carbon dioxide.

A wide range of catalysts can be used in the process of this invention. Typically, the catalyst consists of alumina ($\chi$, $\kappa$, $\gamma$, $\delta$, $\eta$ or $\theta$ configurations) which has, optionally, been activated with silica and/or doped with one or more dopants. Oxides, phosphates, carbonates, halides, sulfides or sulfates of transition, alkali, or alkaline earth metals can be used as dopants. After the application of the dopant, the catalyst can be calcined. Preferred dopants are transition metals such as thorium, chromium, zirconium, uranium, titanium, hafnium, technetium, ruthenium, rhodium, iridium, palladium, platinum, cobalt, cadmium, tungsten and the like, as well as Group I and Group II metals such as lithium, sodium, potassium, magnesium, calcium and barium. More preferred are oxides of lithium, magnesium, calcium, barium, tungsten, sodium, and potassium. Most preferred are oxides of tungsten and potassium. Alternative catalysts can also be utilized, such as spent oil shale, zeolites, activated montmorillonite clay, and the like. Phosphates, carbonates, halides, sulfides and sulfa of the above metals, a few examples of such being cadmium sulfide and potassium carbonate, can also be used. Multiple methods for the production of suitable catalysts are known. Additional information with respect to suitable catalysts and methods of producing such catalysts can be found in U.S. Pat. No. 5,733,836.

The relative amounts of alkyl mercaptan and dialkyl monosulfide produced in the process of this invention are dependent upon the catalyst composition. The impregnation of $\gamma$-alumina with the oxides of transition metals, alkali metals or alkaline earth metals can be used to alter the selectivity of the catalyst with respect to dialkyl monosulfides and alkyl mercaptan. When using a catalyst comprised of (I) $\gamma$-alumina doped with (II) potassium oxide ($K_2O$) and (III) tungsten oxide ($WO_3$), it is desirable to have a weight ratio of (II) to (I) in the range of about 0 gram of (II) per gram of (I) to about 0.1 gram of (II) per gram of (I). If alkyl mercaptan is desired in molar predominance to dialkyl monosulfide, a weight ratio of (II) to (I) in the range of about 0 gram of (II) per gram of (I) to about 0.05 gram of (II) per gram of (I) is more desirable. A ratio in the range of about 0.035 gram of (II) per gram of (I) to about 0.045 gram of (II) per gram of (I) is most desirable to produce alkyl mercaptan in molar predominance to dialkyl monosulfide. If dialkyl monosulfide is desired in greater molar quantities than alkyl mercaptan, a weight ratio of (II) to (I) in the range of from about 0 gram of (II) per gram of (I) to about 0.02 gram of (II) per gram of (I) is more desirable. Most desirable is a (II) to (I) weight ratio in the range of about 0 gram of (II) per gram of (I) to about 0.005 gram of (II) per gram of (I) to obtain a molar predominance of dialkyl monosulfide.

In addition, it is preferable to have a weight ratio of (III) to (I) in the range of about 0 gram of (III) per gram of (I) to about 0.2 gram of (III) per gram of (I). If alkyl mercaptan is desired in greater molar amounts than dialkyl monosulfide, it is more preferable to have a weight ratio of (III) to (I) in the range of about 0 gram of (III) per gram of (I) to about 0.12 gram of (II) per gram of (I). A (III) to (I) weight ratio in the range of about 0.085 gram of (III) per gram of (I) to about 0.095 gram of (III) per gram of (I) is most preferable if alkyl mercaptan is desired in molar predominance to dialkyl monosulfide. If dialkyl monosulfide is desired in greater quantities than alkyl mercaptan, a weight ratio in the range of about 0 gram of (III) per gram of (I) to about 0.04 gram of (III) per gram of (I) is more preferable. In order to produce dialkyl monosulfide in molar predominance over alkyl mercaptan, a weight ratio in the range of about 0 gram of (III) per gram (I) to about 0.005 gram of (III) per gram of (I) is most preferable.

Preferably, the catalyst has a surface area per gram in the range of about 100 to about 300 square meters per gram. More preferably, the catalyst has a surface area in the range of about 150 to about 250 square meters per gram. Most preferably, the catalyst surface area is about 200 square meters per gram. It is preferable that the reaction mixture have a vapor space time in the range of about 0.01 to about 100 seconds. More preferable is a vapor space time in the range of about 0.1 to about 20 seconds. A vapor space time in the range of about 8 seconds to about 12 seconds is most preferable if alkyl mercaptan is desired in greater molar amounts than dialkyl monosulfide. If dialkyl monosulfide is desired in greater molar amounts than alkyl mercaptan, a vapor sa time in the range of about 1 second to about 4 seconds is most preferable.

It is desirable that the catalyst occupy a volume of at least 30% of the reactor volume. It is most desirable that the catalyst occupy a volume of at least 70% of the reactor volume. The volume occupied by the catalyst as referred to here is meant to include the spaces inside the catalyst pores as well as the spaces between catalyst particles. Thus, for example, the catalyst occupies approximately 70% of the volume of a 100 mL graduated cylinder if the cylinder is filled to the 70 mL mark with catalyst particles, even though the actual space occupied by the catalyst may be significantly less. The reaction zone and the catalyst may be used together as a fixed bed or as a fluidized bed.

It is preferable that the temperature in the reaction zone be in the range of about 250° C. to about 450° C. It is more preferable that the temperature in the reaction zone be in the range of about 310° C. to about 410° C. If alkyl mercaptan are desired in greater molar predominance than dialkyl monosulfides, it is most preferable to have a temperature in the range of about 360° C. to about 380° C. If a predominance of dialkyl monosulfide is desired relative to alkyl mercaptan, it is most preferable to have a temperature in the reaction zone in the range of about 340° C. to about 360° C.

A pressure in the reaction zone in the range of about 15 psia to about 500 psia is desirable. More desirable is a pressure in the reaction zone in the range of 50 psia to about 200 psia. A pressure in the range of about 110 psia to about 130 psia is most desirable.

The following example illustrates the low amount of carbonyl sulfide formation in the presence of carbon dioxide. It is not intended to constitute a limitation on the invention, but is presented for purposes of illustration.

EXAMPLE

Approximately 3.1 grams of γ-alumina catalyst were mixed with 27.9 grams of inert alpha alumina. The mixed catalyst was loaded into a reactor with a diameter of 0.5 inches and a length of 17 inches. The methanol, hydrogen sulfide, and carbon dioxide were preheated to the reactor inlet temperature, 385° C. and fed into the reactor as a mixture. The pressure in the reactor was 20 psia. The product effluent was analyzed with an online gas chromatograph for the presence of carbonyl sulfide. The results are shown in the table below.

TABLE

| $[H_2S]/\{[H_2S] + [CO_2]\}$ | Pressure (psia) | VST* (sec) | Temp (° C.) | COS (% vol) |
| --- | --- | --- | --- | --- |
| 1.0 | 20 | 0.11 | 436 | 0.00 |
| 0.5 | 20 | 0.04 | 383 | 0.00 |
| 0.4 | 20 | 0.07 | 450 | 0.00 |
| 0.4 | 20 | 0.08 | 450 | 0.03 |
| 0.3 | 20 | 0.03 | 417 | 0.06 |
| 0.2 | 20 | 0.20 | 360 | 0.00 |

*vapor space time

It is to be understood that the reactants and components referred to by chemical name or by formula anywhere in the specification or claims hereof, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient just as it existed at the time just before it was first contacted, blended or mixed with one or more other substances, components and/or ingredients in accordance with the present disclosure. Thus the fact that a substance, component or ingredient may have lost its original identity through a chemical reaction or transformation through the course of contacting, blending or mixing operations, if conducted in accordance with this disclosure and with the application of common sense and the ordinary skill of a chemist, is wholly immaterial for an accurate understanding and appreciation of the true meaning and substance of this disclosure and the claims thereof.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process for producing alkyl mercaptan and/or dialkyl monosulfide which comprises:
   A) continuously introducing into a reaction zone components comprising (i) an alkanol, (ii) hydrogen sulfide, and (iii) carbon dioxide to form a vapor phase reaction mixture and contacting said mixture in said reaction zone with a solid phase catalyst such that a vapor phase product mixture comprising alkyl mercaptan and/or dialkyl monosulfide is formed, said product mixture also containing carbon dioxide;
   B) continuously withdrawing from said reaction zone a mixture comprising alkyl mercaptan and/or dialkyl monosulfides; and
   C) separating all or a portion of the carbon dioxide present in said vapor phase product mixture, and recycling separated carbon dioxide to A).

2. A process as in claim 1 wherein the mole ratio of (i) to (ii) being continuously introduced into the reaction zone is in the range of about 0.5 mole of (i) per mole of (ii) to about 2.5 moles of (i) per mole of (ii).

3. A process as in claim 1 wherein the mole ratio of (ii) to (iii) being continuously introduced into the reaction zone is in the range of about 0.2 mole of (ii) per mole of (iii) to about 1 mole of (ii) per mole of (iii).

4. A process as in claim 1 wherein the temperature in the reaction zone is in the range of about 250° C. to about 450° C.

5. A process as in claim 1 wherein the catalyst is a composition comprised of (I) aluminum oxide, and optionally (II) an oxide of potassium and/or (III) an oxide of tungsten.

6. A process as in claim 1 wherein the pressure in the reaction zone is in the range of about 15 psia to about 500 psia.

7. A process as in claim 1 wherein (i) is methanol.

8. A process as in claim 1 wherein (i) is methanol, wherein the mole ratio of (i) to (ii) being continuously introduced into the reaction zone is in the range of about 0.5 mole of (i) per mole of (ii) to about 2.5 mole of (i) per mole of (ii), wherein the mole ratio of (ii) to (iii) being continuously introduced into the reaction zone is in the range of about 0.2 mole of (ii) per mole of (iii) to about 1 mole of (ii) per mole of (iii), and wherein the temperature in the reaction zone is in the range of about 250° C. to about 450° C.

9. A process as in claim 1 wherein the catalyst has a surface area in the range of about 100 to about 300 square meters per gram of catalyst.

10. A process as in claim 1 wherein the vapor space time is in the range of about 0.01 to about 100 seconds.

11. A process as in claim 1 wherein the catalyst is a composition comprised of (I) γ-aluminum oxide, (II) potassium oxide, and (III) tungsten oxide, wherein the weight ratio of (II) to (I) is in the range of about 0 gram of (II) per gram of (I) to about 0.1 gram of (II) per gram of (I), and wherein the weight ratio of (III) to (I) is in the range of about 0 gram of (III) per gram of (I) to about 0.2 gram of (III) per gram of (I).

12. A process as in claim 11 wherein (i) is methanol.

13. A process as in claim 1 wherein the mole ratio of the hydrogen sulfide to carbon dioxide being continuously introduced into the reaction zone is in the range of about 0.2 to about 0.8 moles of hydrogen sulfide per mole of carbon dioxide.

14. A process as in claim 1 wherein the mole ratio of (i) to (ii) being continuously introduced into the reaction zone is in the range of about 0.5 mole of (i) per mole of (ii) to about 1.25 mole of (i) per mole of (ii), wherein the mole ratio of (ii) to (iii) being continuously introduced into the reaction zone is in the range of about 0.2 mole of (ii) per mole of (iii) to about 1 mole of (ii) per mole of (iii), and wherein the catalyst is a composition comprised of (I) γ-aluminum oxide, (II) potassium oxide ($K_2O$), and (III) tungsten oxide ($WO_3$), in which the weight ratio of (II) to (I) is in the range of about 0 gram of (II) per gram of (I) to about 0.05 gram of (II) per gram of (I), and in which the weight ratio of (III) to (I) is in the range of about 0 gram of (III) per gram of (I) to about 0.12 gram of (III) per gram of (I), such that at least 10 mole percent of said vapor phase product mixture is alkyl mercaptan.

15. A process as in claim 1 wherein (i) is methanol, wherein the mole ratio of (i) to (ii) being continuously introduced into the reaction zone is in the range of about 0.9 mole of (i) per mole of (ii) to about 1.1 mole of (i) per mole of (ii), wherein the mole ratio of (ii) to (iii) being continuously introduced into the reaction zone is in the range of about 0.4 mole of (ii) per mole of (iii) to about 0.6 mole of (ii) per mole of (iii), wherein the temperature in the reaction zone is in the range of about 360° C. to about 380° C., wherein the pressure in the reaction zone is in the range of about 110 psia to about 130 psia, wherein the catalyst is a composition comprised of (I) γ-aluminum oxide, (II) potassium oxide ($K_2O$), and (III) tungsten oxide ($WO_3$), wherein the weight ratio of (II) to (I) is in the range of about 0.035 gram of (II) per gram of (I) to about 0.045 gram of (II) per gram of (I), wherein the weight ratio of (III) to (I) is in the range of about 0.085 gram of (III) per gram of (I) to about 0.095 gram of (III) per gram of (I), wherein the catalyst has a surface area of about 200 square meters per gram of catalyst, and wherein the vapor space time is in the range of about 8 seconds to about 12 seconds.

16. A process as in claim 15 wherein all or a portion of the carbon dioxide present in said vapor phase product mixture comprising methyl mercaptan and, optionally, dimethyl sulfide is separated from said vapor phase product mixture, and recycled to A).

17. A process as in claim 1 wherein the mole ratio of (i) to (ii) being continuously fed into the reaction zone is in the range of about 1 mole of (i) per mole of (ii) to about 2.5 moles of (i) per mole of (ii), wherein the mole ratio of (ii) to (iii) being continuously fed into the reaction zone is in the range of about 0.2 mole of (ii) per mole of (iii) to about 1 mole of (ii) per mole of (iii), and wherein the catalyst is a composition comprised of (I) γ-aluminum oxide, (II) potassium oxide, and (III) tungsten oxide, in which the weight ratio of (II) to (I) is in the range of about 0 gram of (II) per gram of (I) to about 0.02 gram of (II) per gram of (I), and in which the weight ratio of (III) to (I) is in the range of about 0 gram of (III) per gram of (I) to about 0.04 gram of (III) per gram of (I), such that at least 10 mole percent of said vapor phase product mixture is dialkyl monosulfide.

18. A process as in claim 1 wherein (i) is methanol, wherein the mole ratio of (i) to (ii) being continuously introduced into the reaction vessel is in the range of about 1.9 moles of (i) per mole of (ii) to about 2.1 moles of (i) per mole of (ii), wherein the mole ratio of (ii) to (iii) being continuously introduced into the reaction vessel is in the range of about 0.2 mole of (ii) per mole of (iii) to about 0.4 mole of (ii) per mole of (iii), wherein the temperature in the reaction vessel is in the range of about 340° C. to about 360° C., wherein the pressure in the reaction vessel is in the range of about 110 psia to about 130 psia, wherein the catalyst is a composition comprised of (I) γ-aluminum oxide, (II) potassium oxide ($K_2O$), and (III) tungsten oxide ($WO_3$), in which the weight ratio of (II) to (I) is in the range of about 0 gram of (II) per gram of (I) to about 0.005 gram of (II) per gram of (I), and in which the weight ratio of (III) to (I) is in the range of about 0 gram of (III) per gram of (I) to about 0.005 gram of (III) per gram of (I), wherein the surface area of the catalyst is about 200 square meters per gram of catalyst, and wherein the vapor space time is in the range of about 1 second to about 4 seconds.

19. A process as in claim 18 wherein all or a portion of the carbon dioxide present in said vapor phase product mixture comprising dimethyl sulfide and, optionally, methyl mercaptan is separated from said vapor phase reaction mixture and recycled to A).

20. A process for producing alkyl mercaptan and/or dialkyl monosulfide, which process comprises:
    A) continuously introducing into a reaction zone components comprising (i) an alkanol, (ii) hydrogen sulfide, and (iii) carbon dioxide to form a vapor phase reaction mixture and contacting said mixture with a solid phase catalyst such that a vapor phase product mixture comprising alkyl mercaptan and/or dialkyl monosulfide and carbon dioxide is formed in said reaction zone;
    B) continuously withdrawing said vapor phase product mixture from said reaction zone;
    C) separating carbon dioxide from said withdrawn vapor phase product mixture; and
    D) recycling carbon dioxide from C) to A).

21. A process as in claim 20 wherein the mole ratio of (i) to (ii) being continuously introduced into the reaction zone is in the range of about 0.5 mole of (i) per mole of (ii) to about 2.5 moles of (i) per mole of (ii), and wherein the mole ratio of (ii) to (iii) being continuously introduced into the reaction zone is in the range of about 0.2 mole of (ii) per mole of (iii) to about 1 mole of (ii) per mole of (iii).

22. A process as in claim 20 wherein (i) is methanol.

23. A process as in claim 22 wherein the mole ratio of (i) to (ii) being continuously introduced into the reaction zone is in the range of about 0.5 mole of (i) per mole of (ii) to about 2.5 moles of (i) per mole of (ii), and wherein the mole ratio of (ii) to (iii) being continuously introduced into the reaction zone is in the range of about 0.2 mole of (ii) per mole of (iii) to about 1 mole of (ii) per mole of (iii).

24. A process as in claim 20 wherein (i) is methanol, wherein the mole ratio of (i) to (ii) being continuously introduced into the reaction zone is about 1 mole of (i) per mole of (ii), wherein the mole ratio of (ii) to (iii) being continuously introduced into the reaction zone is in the range of about 0.4 mole of (ii) per mole of (iii) to about 0.6 mole of (ii) per mole of (iii), wherein the temperature in the reaction zone is in the range of about 360° C. to about 380° C., wherein the pressure in the reaction zone is in the range of about 110 psia to about 130 psia, wherein the catalyst is a composition comprised of (I) γ-aluminum oxide, (II) potassium oxide (K$_2$O), and (III) tungsten oxide (WO$_3$), in which the weight ratio of (II) to (I) is in the range of about 0.035 gram of (II) per gram of (I) to about 0.045 gram of (II) per gram of (I), and in which the weight ratio of (III) to (I) is in the range of about 0.085 gram of (III) per gram of (I) to about is about 0.095 gram of (III) per gram of (I), wherein the catalyst surface area is about 200 square meters per gram of catalyst, wherein the vapor space time is in the range of about 8 seconds to about 12 seconds, and wherein the reaction products comprise methyl mercaptan, and optionally, dimethyl sulfide.

25. A process as in claim 20 wherein (i) is methanol, wherein the mole ratio of (i) to (ii) being introduced into the reaction zone is in the range of about 1.9 moles of (i) per mole of (ii) to about 2.1 mole of (i) per mole of (ii), wherein the mole ratio of (ii) to (iii) being introduced into the reaction zone is in the range of about 0.2 mole of (ii) per mole of (iii) to about 0.4 mole of (ii) per mole of (iii), wherein the temperature in the reaction zone is in the range of about 340° C. to about 360° C., wherein the pressure in the reaction zone is in the range of about 110 psia to about 130 psia, wherein the catalyst is a composition comprised of (I) γ-aluminum oxide, (II) potassium oxide, and (III) tungsten oxide, in which the weight ratio of (II) to (I) is in the range of about 0 gram of (II) per gram of (I) to about 0.005 gram of (II) per gram of (I), and in which the weight ratio of (III) to (I) is in the range of about 0 gram of (III) per gram of (I) to about 0.005 gram of (III) per gram of (I), wherein the catalyst surface area is about 200 square meters per gram of catalyst, wherein the vapor space time is in the range of about 1 second to about 4 seconds, and wherein the reaction products comprise dimethyl sulfide, and optionally, methyl mercaptan.

26. A process for producing alkyl mercaptan and/or dialkyl monosulfide which comprises:

A) continuously introducing into a reaction zone components comprising (i) an alkanol, (ii) hydrogen sulfide, and (iii) carbon dioxide in proportions of about 1 to about 5 moles of carbon dioxide per mole of hydrogen sulfide, to form a vapor phase reaction mixture and contacting said mixture in said reaction zone with a solid phase catalyst such that a vapor phase product mixture comprising alkyl mercaptan and/or dialkyl monosulfide is formed; and B) continuously withdrawing from said reaction zone a mixture comprising alkyl mercaptan and/or dialkyl monosulfides.

27. A process as in claim 26 wherein the alkanol and hydrogen sulfide are being introduced into the reaction zone in proportions of about 0.5 to about 2.5 moles of alkanol per mole of hydrogen sulfide.

28. A process as in claim 26 wherein the carbon dioxide and hydrogen sulfide are being introduced into the reaction zone in proportions of about 1.25 to about 5 moles of carbon dioxide per mole of hydrogen sulfide.

29. A process as in claim 28 wherein the alkanol and hydrogen sulfide are being introduced into the reaction zone in proportions of about 0.5 to about 2.5 moles of alkanol per mole of hydrogen sulfide.

30. A process as in claim 26 wherein the carbon dioxide and hydrogen sulfide are being introduced into the reaction zone in proportions of about 1.67 to about 2.5 moles of carbon dioxide per mole of hydrogen sulfide.

31. A process as in claim 26 wherein the carbon dioxide and hydrogen sulfide are being introduced into the reaction zone in proportions of about 2.5 to about 5 moles of carbon dioxide per mole of hydrogen sulfide.

\* \* \* \* \*